(12) United States Patent
Nace

(10) Patent No.: US 8,376,974 B2
(45) Date of Patent: Feb. 19, 2013

(54) KNEE ORTHOSIS SWING ASSIST MECHANISM

(76) Inventor: Richard A. Nace, Miami, FL (US)

( * ) Notice: Subject to any disclaimer, the term of this patent is extended or adjusted under 35 U.S.C. 154(b) by 0 days.

(21) Appl. No.: 13/178,447

(22) Filed: Jul. 7, 2011

(65) Prior Publication Data

US 2011/0282255 A1    Nov. 17, 2011

Related U.S. Application Data

(60) Continuation-in-part of application No. 12/366,925, filed on Feb. 6, 2009, now abandoned, and a division of application No. 11/556,557, filed on Nov. 3, 2006, now Pat. No. 7,608,051.

(51) Int. Cl.
*A61F 5/00* (2006.01)
*A61H 1/00* (2006.01)

(52) U.S. Cl. ............................. 602/16; 601/35

(58) Field of Classification Search ............ 602/26, 602/23, 16, 5, 1; 601/1, 23, 33, 34, 35
See application file for complete search history.

(56) References Cited

U.S. PATENT DOCUMENTS

| | | | | |
|---|---|---|---|---|
| 3,453,663 A | * | 7/1969 | Minor | 623/40 |
| 4,433,679 A | * | 2/1984 | Mauldin et al. | 602/16 |
| 4,574,789 A | * | 3/1986 | Forster | 602/32 |
| 4,606,542 A | * | 8/1986 | Segal | 482/124 |
| 4,991,571 A | | 2/1991 | Kausek | |
| 5,213,094 A | * | 5/1993 | Bonutti | 601/33 |
| 5,330,418 A | | 7/1994 | Townsend et al. | |
| 6,039,709 A | | 3/2000 | Bzoch | |
| 6,537,237 B1 | | 3/2003 | Hopkins et al. | |
| 7,060,045 B2 | | 6/2006 | Mason et al. | |
| 7,306,572 B2 | | 12/2007 | Ceriani et al. | |
| 7,311,687 B2 | | 12/2007 | Hoffmeier et al. | |
| 2002/0133108 A1 | * | 9/2002 | Jagodzinski | 602/16 |
| 2003/0144620 A1 | * | 7/2003 | Sieller et al. | 602/5 |
| 2006/0206043 A1 | * | 9/2006 | Yakimovich et al. | 602/16 |

* cited by examiner

*Primary Examiner* — Patricia Bianco
*Assistant Examiner* — Tarla Patel
(74) *Attorney, Agent, or Firm* — Larson & Larson, P.A.; Frank Liebenow; Justin P. Miller

(57) ABSTRACT

A knee orthosis gait swing assist mechanism is provided having an adjustable portion and upper and lower fulcrum points, each of the upper and lower fulcrum points attaching opposing ends of an elastic band, the elastic band stretching over the adjustable portion.

18 Claims, 12 Drawing Sheets

KNEE ORTHOSIS SWING ASSIST MECHANISM

PRIOR APPLICATIONS

This application is a continuation-in-part application of U.S. Ser. No. 12/366,925, filed on Feb. 6, 2009, now abandoned, which is a divisional application of U.S. Ser. No. 11/556,557, filed Nov. 3, 2006, now patented as U.S. Pat. No. 7,608,051.

FIELD OF THE INVENTION

The invention relates to knee braces. More particularly, it refers to structural parts used with knee braces. And with more particularity, it refers to a knee brace swing assist mechanism used to assist in flexion and extension and improve gait.

BACKGROUND OF THE INVENTION

Orthotic devices and appliances commonly referred to as "orthotics," have been utilized for many years by orthotists, physical therapists, and occupational therapists to assist in the rehabilitation of patient's joints and associated limbs or adjacent skeletal parts of the patient's body.

Webster's New College Dictionary defines "orthotics" as a branch of mechanical and medical science that deals with the support and bracing of weak or ineffective joints or muscles.

Orthotics or limb braces have been designed to support and protect the joint, alleviate pain associated with joint movement, and to rehabilitate the joint over time with orthotic use.

Primary osteoarthritis is usually related to aging. With aging, the water content of the cartilage increases and the protein makeup of the cartilage degenerates. Repetitive use of the joints over the years can irritate and inflame the cartilage, causing joint pain and swelling. Eventually, cartilage begins to degenerate by flaking or forming tiny crevasses. In advanced cases, there is a total loss of cartilage cushion between the femur and tibia bones at the knee joint, leading to diminished joint space on the affected side of the knee resulting in pain and limitation of joint mobility. Inflammation of the cartilage also can stimulate new bone outgrowths (spurs) to form around the joints causing increased pain and joint inflammation.

Osteoarthritis is often described as "wear and tear" arthritis, as it is highly correlated to age. Osteoarthritis is one of the most frequent causes of physical disability among adults. More than 20 million people in the US have the disease. By 2030, 20 percent of Americans, about 70 million people, will have passed their 65$^{th}$ birthday and will be at risk for osteoarthritis.

Osteoarthrosis is a condition where the joint is affected by degeneration. Osteoarthritis implies the same meaning, but the "it is" adds the meaning that the joint is inflamed. The two terms are often used interchangeably.

Joint replacement surgery of the knee is the surgical treatment for osteoarthrosis or osteoarthritis. It is best to delay knee joint replacement surgery as long as possible, as a total knee replacement may need to be replaced in ten to twenty years. It is a major surgery which requires considerable rehabilitation therapy to restore full function.

Exercise, weight loss if needed, and the use of anti-inflammatory medications and analgesics are often prescribed to assist the patient in managing the pain associated with osteoarthritis. Minimizing the progression of the damage to the cartilage of the knee joint and preventing the formation of bone spurs from "bone on bone" during knee joint bending is an important part of patient care.

The actual pain of osteoarthritis or osteoarthrosis comes from wearing away of the soft cartilage that pads the junction of the femur (upper leg bone of the knee) and the tibia (lower leg bone of the knee). With irritation of the joint, bone spurs can form causing bits of bone and cartilage to break off which float inside the joint space further irritating the knee. The most common form of osteoarthritis or osteoarthrosis is unicompartmental, meaning that only one of the three compartments of the knee joint are significantly affected by the loss of cartilage padding. The medial compartment of the knee is on the inside of the center line of the body. The lateral compartment of the knee is on the outside plane of the body, and the patellar compartment is in the center top of the knee behind the patella or knee cap. The majority of cases of osteoarthritis are medial compartment degeneration where the cartilage or cushioning of the knee joint has significantly deteriorated. The knee then becomes imbalanced, with the knee bowing outwards. This is often called a "bowleg" condition. A "bowleg" (genu varum), commonly referred to as a varus deformity of the knee joint, places significant force on the medial compartment of the knee, which aggravates the pain associated with osteoarthritis when the patient walks, bends the knee, or stands up.

As the cartilage or padding of the knee joint on the lateral compartment cartilage is worn away, the knee will deform abnormally bending inwards at the knee joint giving the patient a knock kneed appearance. This is referred to as a valgus deformity of the knee joint.

Osteoarthritis knee braces are designed to do two things: first, correct the abnormal bending of the knee joint inwards or outwards (varus or valgus correction). Secondly, many osteoarthritis knee orthotics or braces are designed to prevent the "bone on bone" contact of the femur and tibia bones in the medial or lateral compartment of the knee joint as the patient bears weight during ambulation. This action of lifting femur, pulling down the tibia or keeping the femur and tibia bones from coming in contact during the straightening of the knee during heel strike is often called "unloading" the knee joint. By "unloading" the knee joint, the constant irritation of the degenerated cartilage in the affected compartment of the knee (medial or lateral) can lead to a significant reduction in pain and further injury to the knee joint. Osteoarthritis knee braces also provide improved alignment of the upper and lower aspects of the knee joint by preventing the bending inwards or outwards of the knee joint during gait. These two features, unloading and alignment are provided by most of the osteoarthritis knee orthotics available in today's market.

The majority of knee orthotics available to treat osteoarthritis of the knee utilizes a single upright attached to an upper thigh cuff and lower shin cuff. The upright is located on the side of the collapsed compartment of the knee; i.e. medial side for medial compartment osteoarthritis. The attached cuffs "offload" the biomechanical force on the affected compartment of the knee by increasing the joint space on the affected side as the knee goes from flexion to extension. Many osteoarthritis braces use an angled strap from the upper part of the brace that goes across the opposite side of the knee joint from the side bar or upright to improve the alignment of the knee during ambulation to better balance the forces on the knee during gait more evenly. The strap provides a three point leverage that pulls the knee joint into proper alignment during gait. A combination of the single sided upright with cuff attachments and the valgus producing strap have shown to provide improved performance in severe genu varum osteoarthritis. However, it is difficult to set the desired degrees of flexion and extension.

Although many of the existing knee braces containing locking hinge assemblies serve their intended purpose, difficulty in ease of setting the desired degrees of flexion and extension continues to be a problem. Improvement is needed whereby a swing assist mechanism is provided for any type of knee brace, either having flexion and extension degree setting points or without such setting points, but which assists the knee brace to swing outward and then return for improving knee performance and correcting abnormal gait in a patient using such knee brace.

SUMMARY OF THE INVENTION

The present invention is dynamic swing assist mechanism used with or in any type of knee brace having at least one upright. The mechanism can have desired degree of flexion and extension or not. Further, the mechanism can be attached to an outside portion of a hinge of the knee brace along the at least one upright, made integral as part of the hinge or made integral has part of the at least one upright. Still further, two dynamic swing assist mechanisms, configured as mentioned directly above, can be employed in a knee brace having a pair of uprights.

In knee braces that unload the pressure on an affected side of a knee joint, balance the joint space on both sides of the knee during ambulation and improve knee joint alignment, the swing assist can then be adjusted as the condition of the knee improves or deteriorates to maintain joint space balance, change the unloading effect on the affected side of the knee joint, improve knee joint alignment during gait and correct improper gait.

As alignment of the knee changes (joint space balance), the swing assist mechanism of the knee brace is adjusted so that joint space balance is continually maintained with joint rehabilitation. The current invention in one embodiment achieves this significant improvement with an adjustable dynamic fulcrum to allow the clinician to quickly and easily adjust the brace to maintain joint space balance as needed during the knee rehabilitation process.

As an example, the present invention can accomplish the desired result of joint space balance by providing a lateral polycentric hinge and a medial unicentric hinge component positionable respectively laterally and medially adjacent the knee joint. A shin cuff is circumscribable about on one front or back side of the lower leg. The lower member of each hinge is attached to a lateral and medial upright element respectively integral with the shin cuff. A thigh cuff is aligned with one of the front or back sides of patient's thigh, above the knee joint. The thigh cuff has a lateral and medial element extending downwardly to engage a top hinge arm of the lateral and medial hinge respectively. An adjustable swing assist mechanism, such as a dynamic fulcrum hinge component, is then used to assist during leg extension and flexion (i.e., during walking), squatting and sitting. By moving setting blocks different degrees of tension is introduced into the polycentric lateral hinge.

BRIEF DESCRIPTION OF THE DRAWINGS

This invention can be best understood by those having ordinary skill in the art by reference to the following detailed description, when considered in conjunction with the accompanying drawings in which.

DETAILED DESCRIPTION OF THE INVENTION

Figure 1:
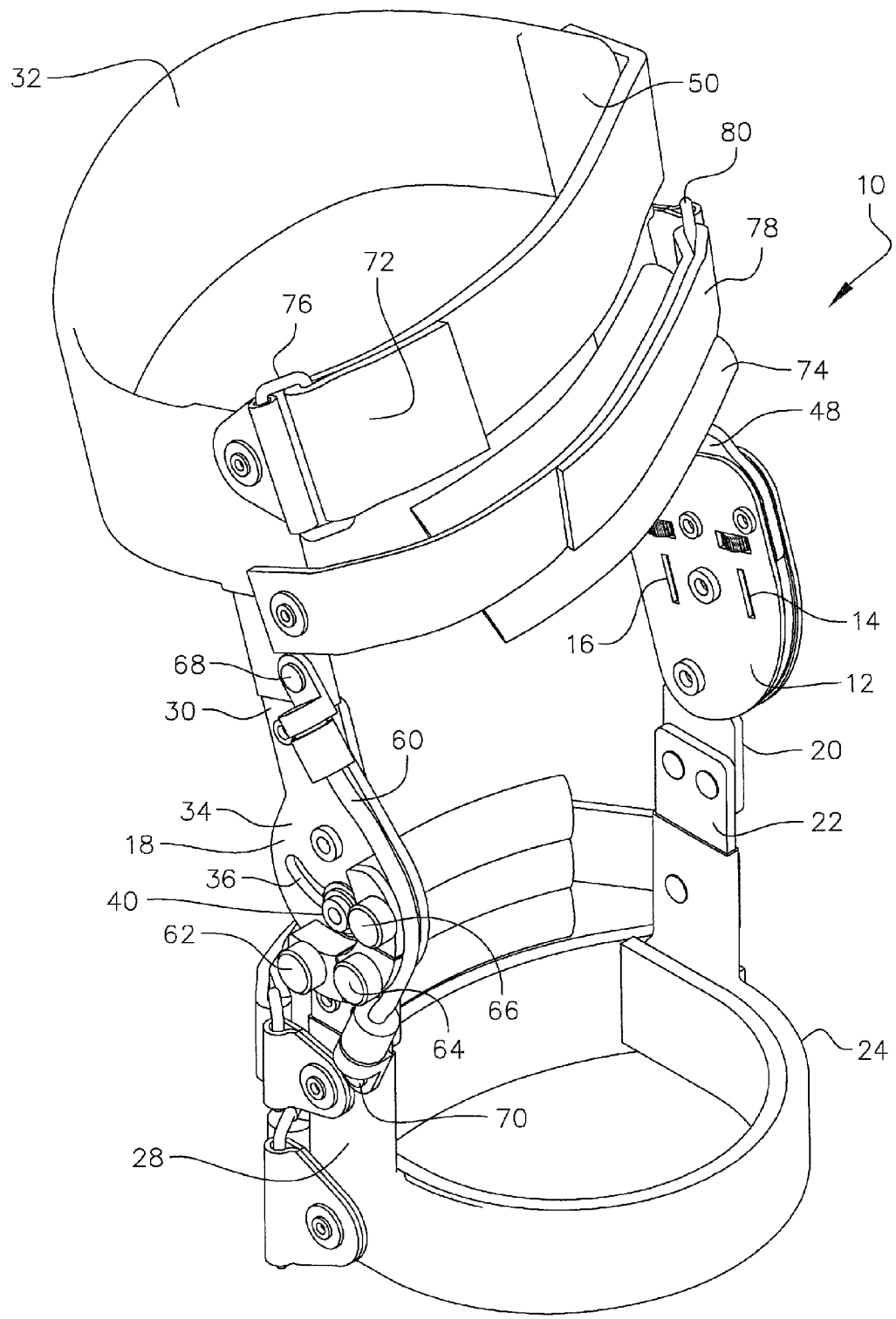
FIG. 1 is a lateral side perspective view of a knee brace employing a first embodiment of the swing assist mechanism of this invention.

Throughout the following detailed description the same reference numerals refer to the same elements in all figures.

Figure 2:
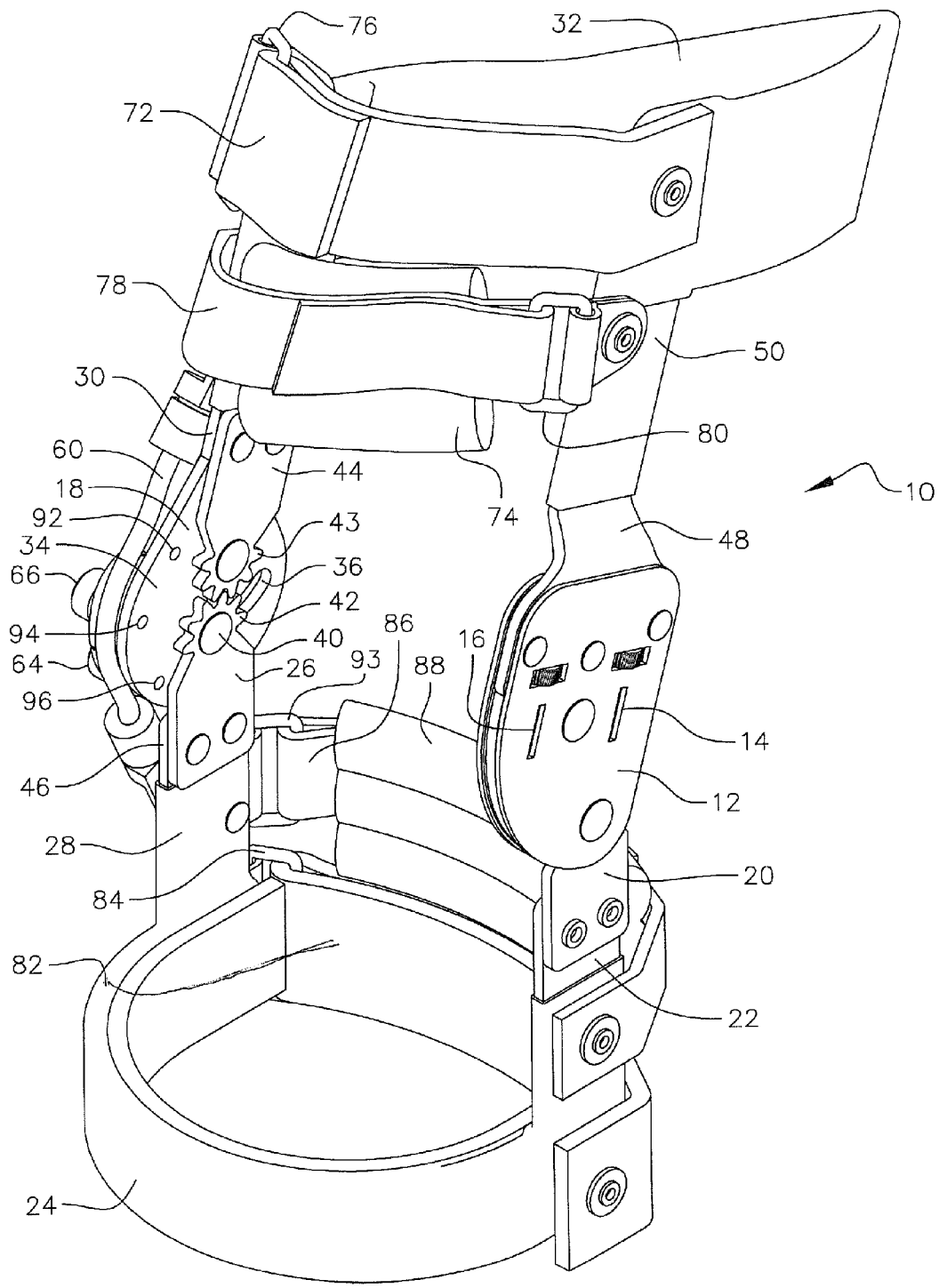
FIG. 2 is a medial side perspective view of the mechanism of FIG. 1.
Figure 3:
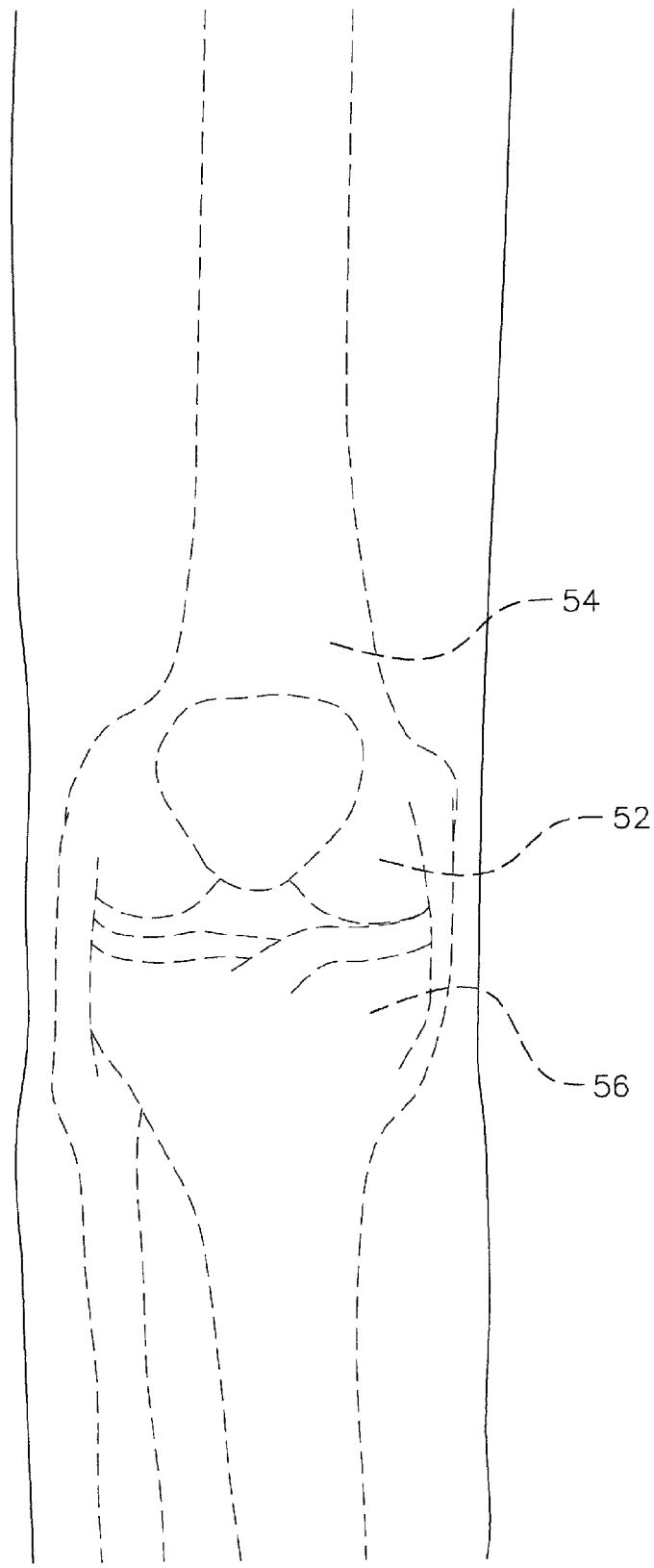
FIG. 3 is a front view of a knee with a hidden view of the patella out of alignment.

Referring to FIGS. 1 and 2, the osteoarthritis knee orthosis 10 (hereafter identified as OA), has a medial unicentric hinge 12 with flexion stop 14 and extension stop 16 at any setting. The medial unicentric hinge 12 is substantially parallel to a lateral polycentric adjustable tension offloading hinge 18. The bottom end 20 of medial hinge 12 is attached to a first upright member 22 integral with a knee ring 24. A lower gear plate 26 of lateral hinge 18 is attached to a second upright member 28 integral with knee ring 24.

An upper arm 30 of the lateral hinge 18 connects at an upper end to a flexible upper thigh cuff 32. A lower portion of the lateral hinge broadens out to a slotted hinge connector plate 34. A slot 36, in connector plate 34 contains a transverse shaft on rivet 40. The rivet 40 attaches a first star gear 42 to an inside surface of the slotted connector plate 34. A second star gear 43 is integral with a gear plate 44 attached to an inner surface of upper arm 30.

Figure 4:
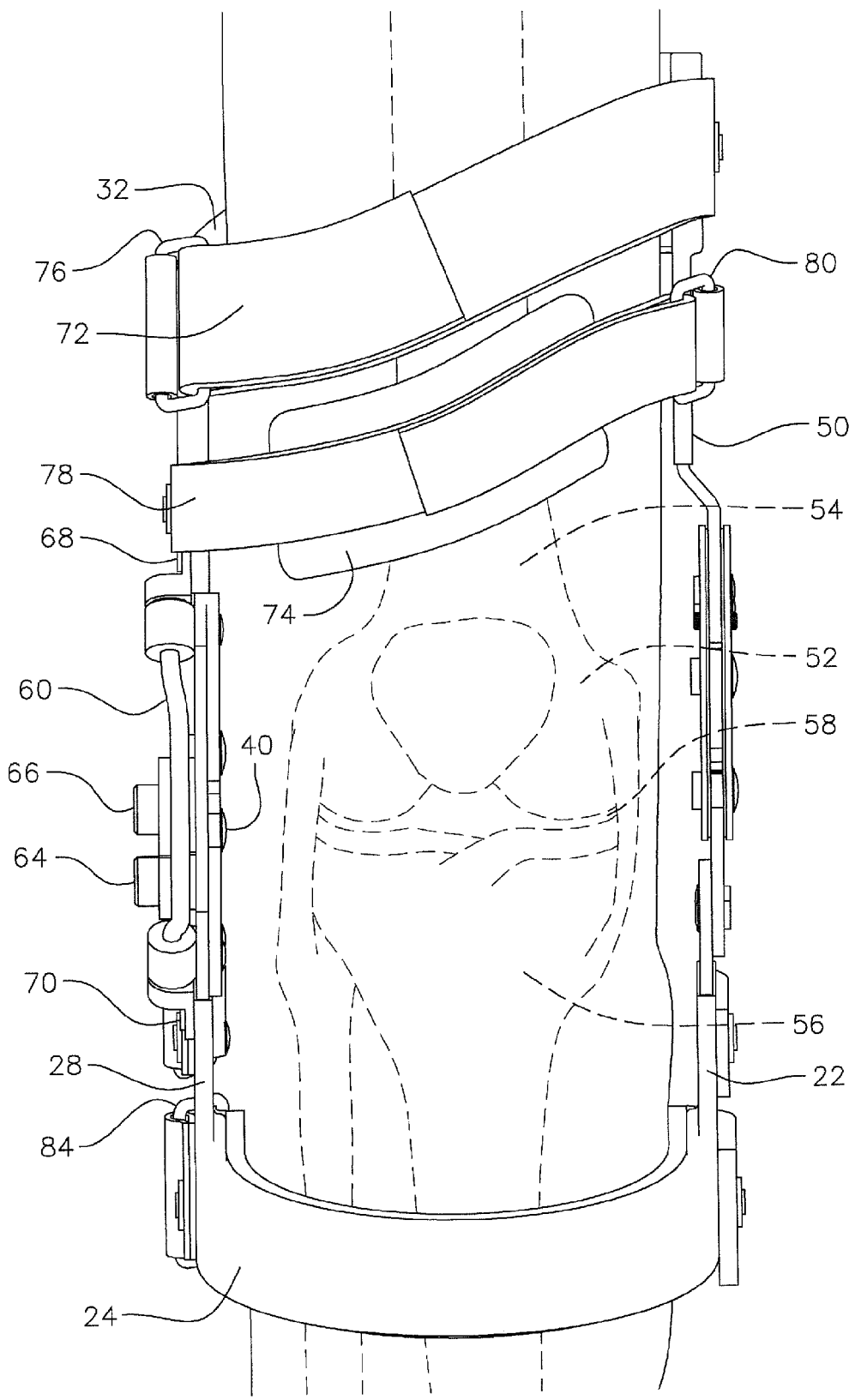
FIG. 4 is a front view of a knee with a hidden view of the patella with a knee brace utilizing the swing assist mechanism of this invention in place.

An upper arm 48 of the medial hinge 12 is attached at its top end 50 to the flexible upper thigh cuff 32. Medial hinge 12 is a KWIK-SET design set forth in U.S. Pat. No. 6,039,709, incorporated herein by reference. The upper arm 48 of medial hinge 12 is significantly longer than the upper arm 30 of the lateral hinge set 18; about 1½ inches in the medium size. The longer length of medial upper arm 48 compared to the upper arm 30 of the lateral hinge 18 encourages unloading of force from the medial compartment of the knee by lifting the medial side 52 of the femur 54 off of the tibia 56 with weight bearing during full leg extension. See the gap 58 shown in FIG. 4.

The lower medial side upright 22 and lower lateral side upright 28 are equivalent in length. The medial upper arm 48 is set back at an angle of approximately 15° to 20° with the leg straight whereas upper lateral arm 30 and lower lateral upright 28 are in a relatively straight alignment with the hinge when the leg is straight. The offset portion of arm 48 improves knee alignment from 20° of flexion to full extension of the knee joint and prevents "reverse Screw Home Mechanism" rotation of the knee.

As shown, the various elements are held together by rivets such as rivet 40. Other equivalent means of attachment could be substituted for the rivets.

Figure 5A:
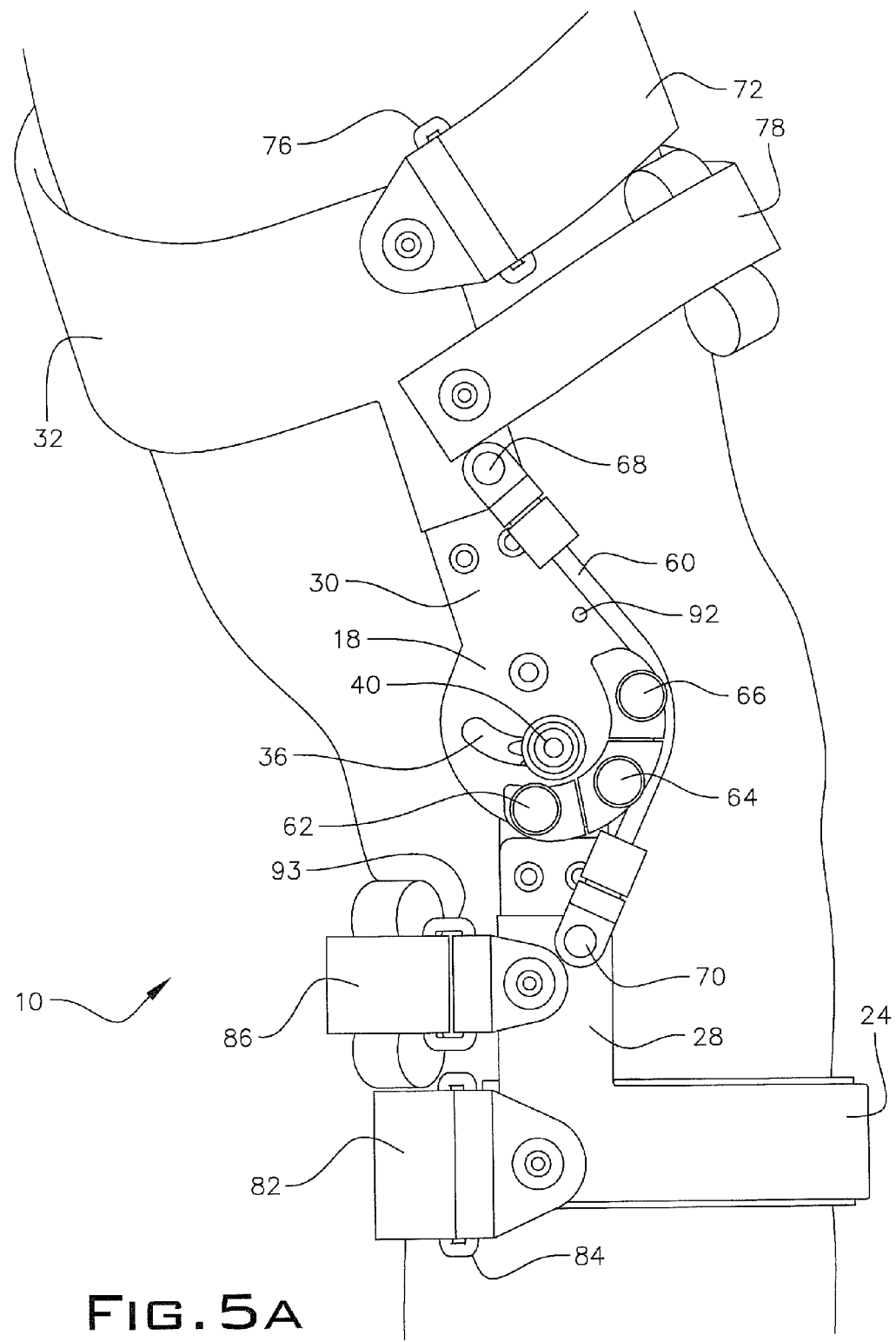
FIG. 5A is a lateral side view of a knee brace hinge assembly and the novel swing assist mechanism of FIG. 1 on an extended leg of a patient.
Figure 5B:
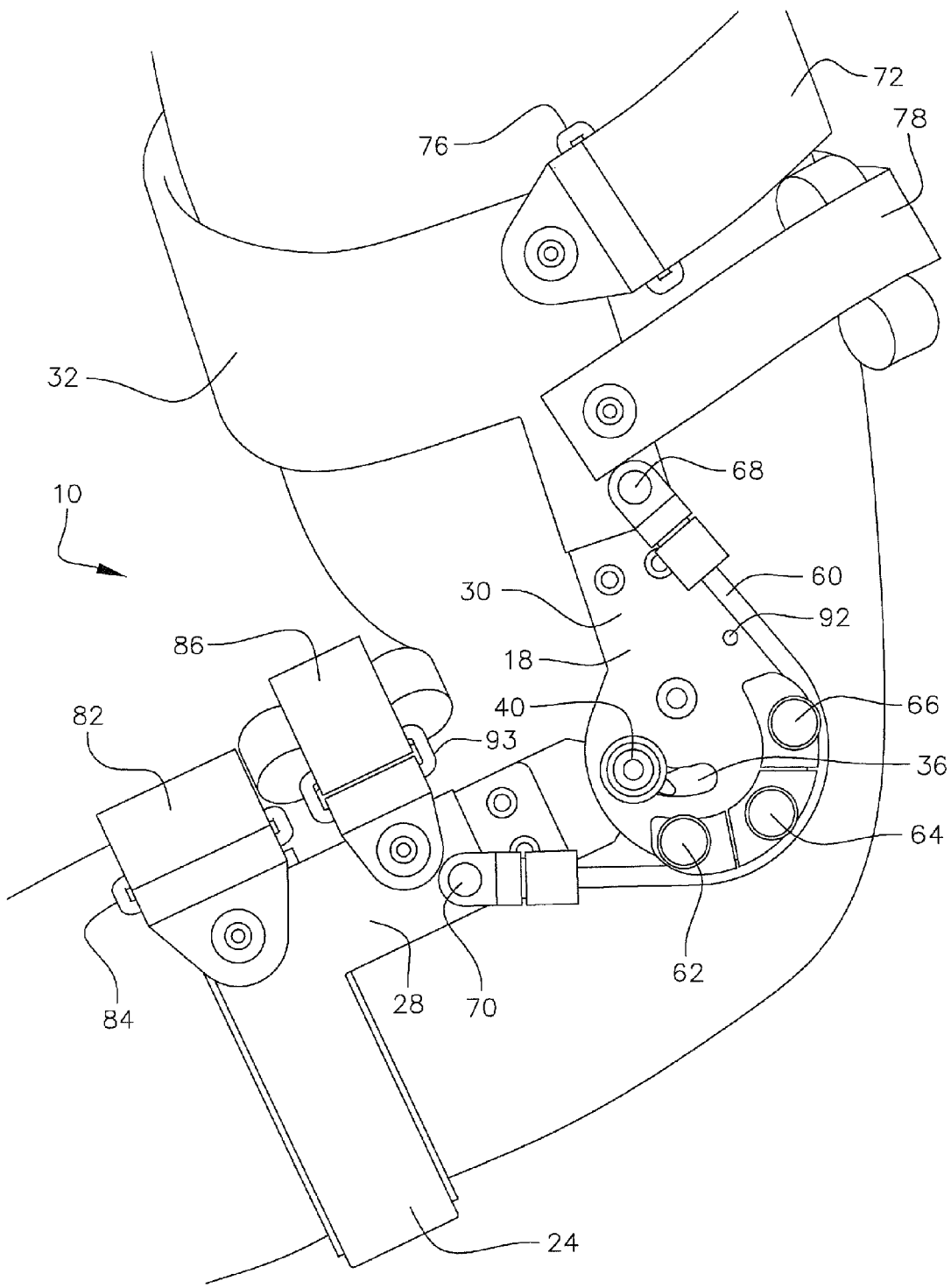
FIG. 5B is a lateral side view of a knee brace hinge assembly and the novel swing assist mechanism of FIG. 5A with the patient's knee in a bent position.

On polycentric hinge 18, an elastic band 60 attaches at a lower end on the outside of the second upright member 28 at fulcrum point 70 and travels adjacent fulcrum blocks 62, 64 and 66 to terminate at fulcrum 68. The dynamic tension of the fulcrum 68 can be set by the fitter by using fulcrum blocks 62, 64 and 66. In addition, various elastic bands 60 with varying elastic properties can be substituted to allow the fitter to adjust the dynamic fulcrum with multiple tension forces. The dynamic adjustable fulcrum is derived from the elastic band 60 positioned from the lower fulcrum point 70 and stretched over fulcrum blocks 62, 64 and 66 at the lateral hinge as the knee bends. See FIG. 5B. The adjustable dynamic fulcrum is used to provide a dynamic tension force at the knee joint that can be used to balance the joint space 58 between the medial and lateral compartments and to provide optimal alignment of the knee with the OA 10 brace.

Figure 6A:
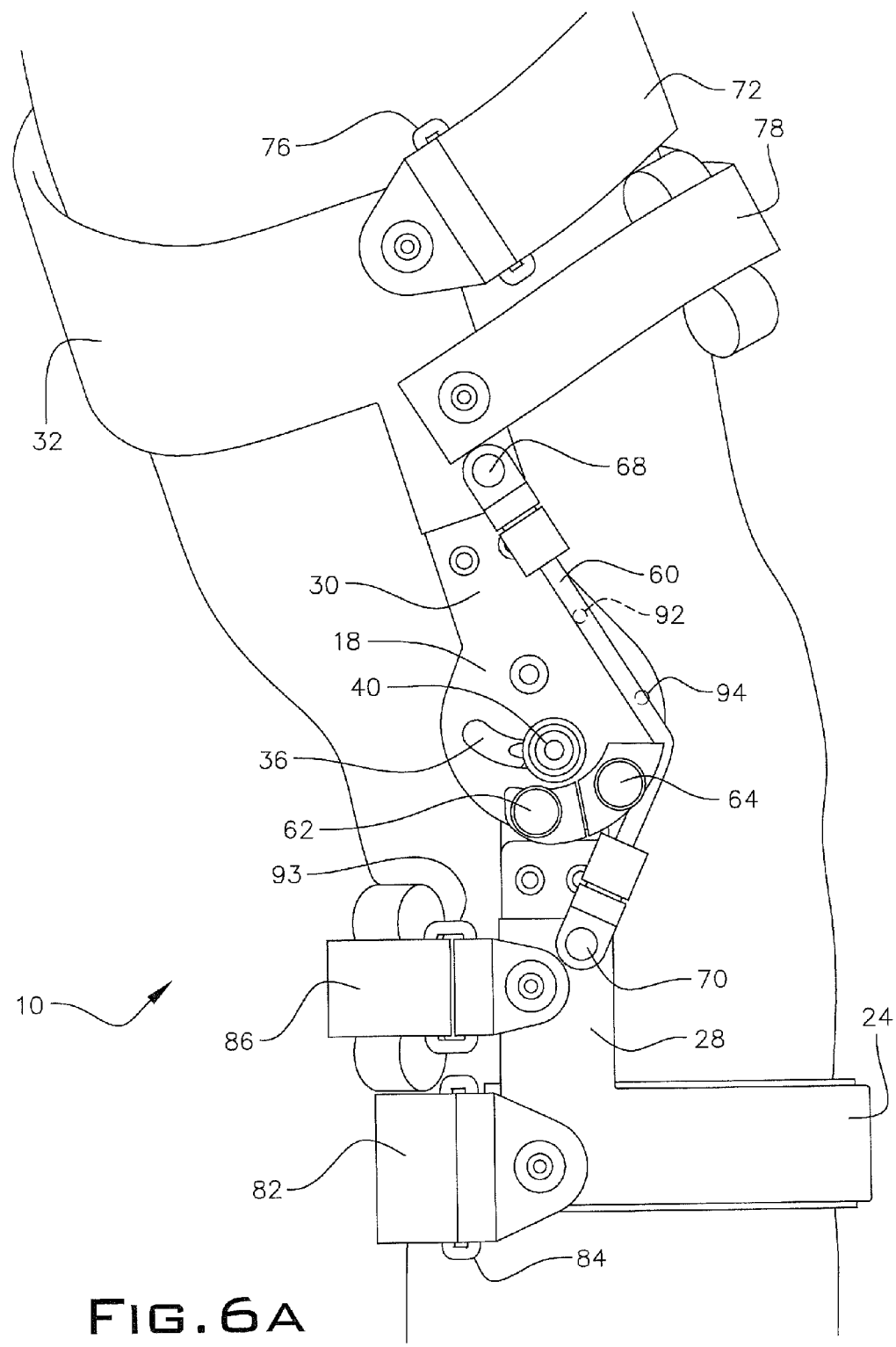
FIG. 6A is a lateral side view of a knee brace hinge assembly and the novel swing assist mechanism of FIG. 1 on an extended leg of a patient with only two fulcrum blocks in place.
Figure 6B:
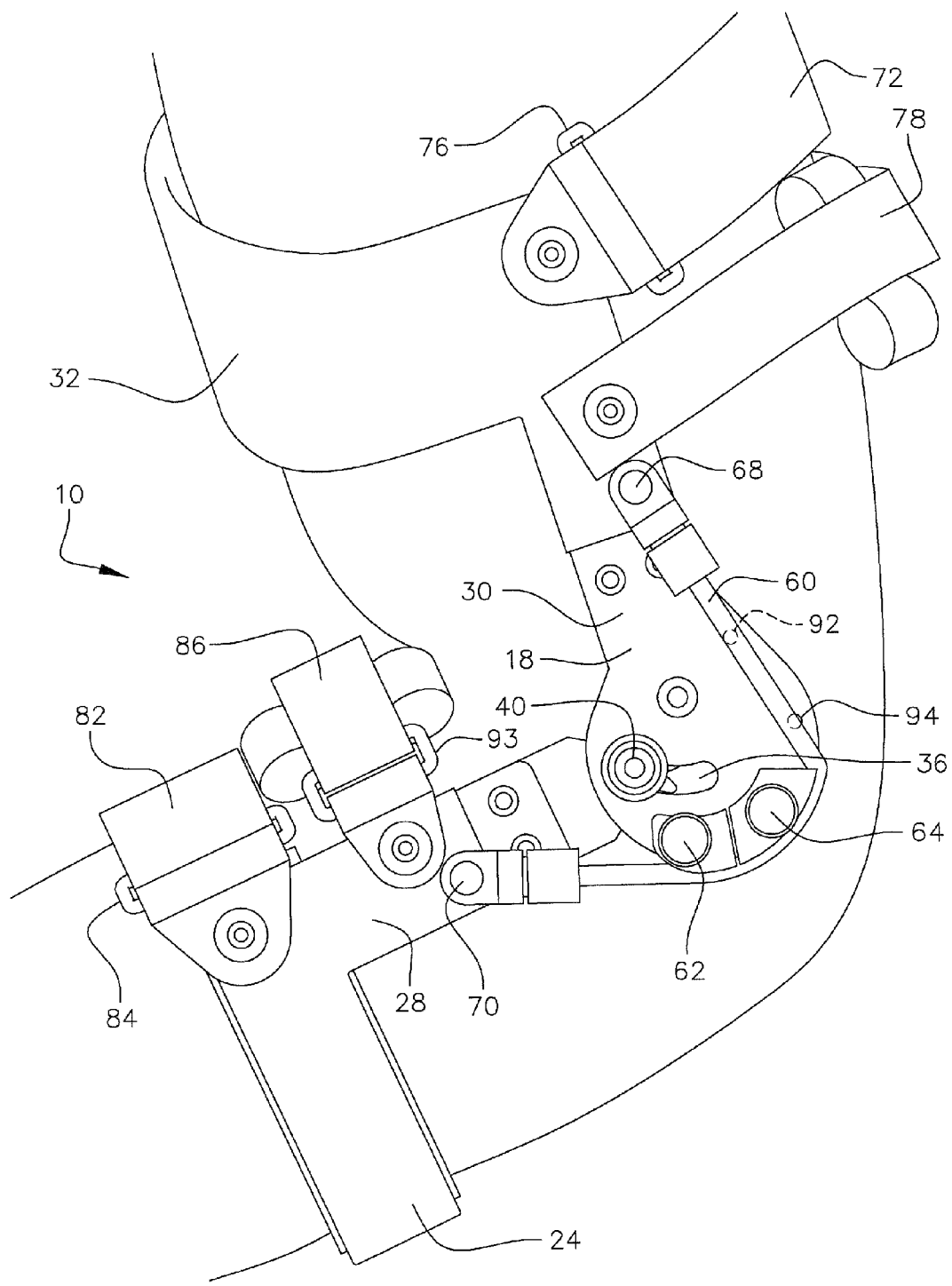
FIG. 6B is a lateral side elevational view according to FIG. 6A with the patient's knee bent.

FIGS. 6A and 6B show alignment using only two fulcrum blocks, 62 and 64, on the polycentric hinge 18.

Figure 7A:
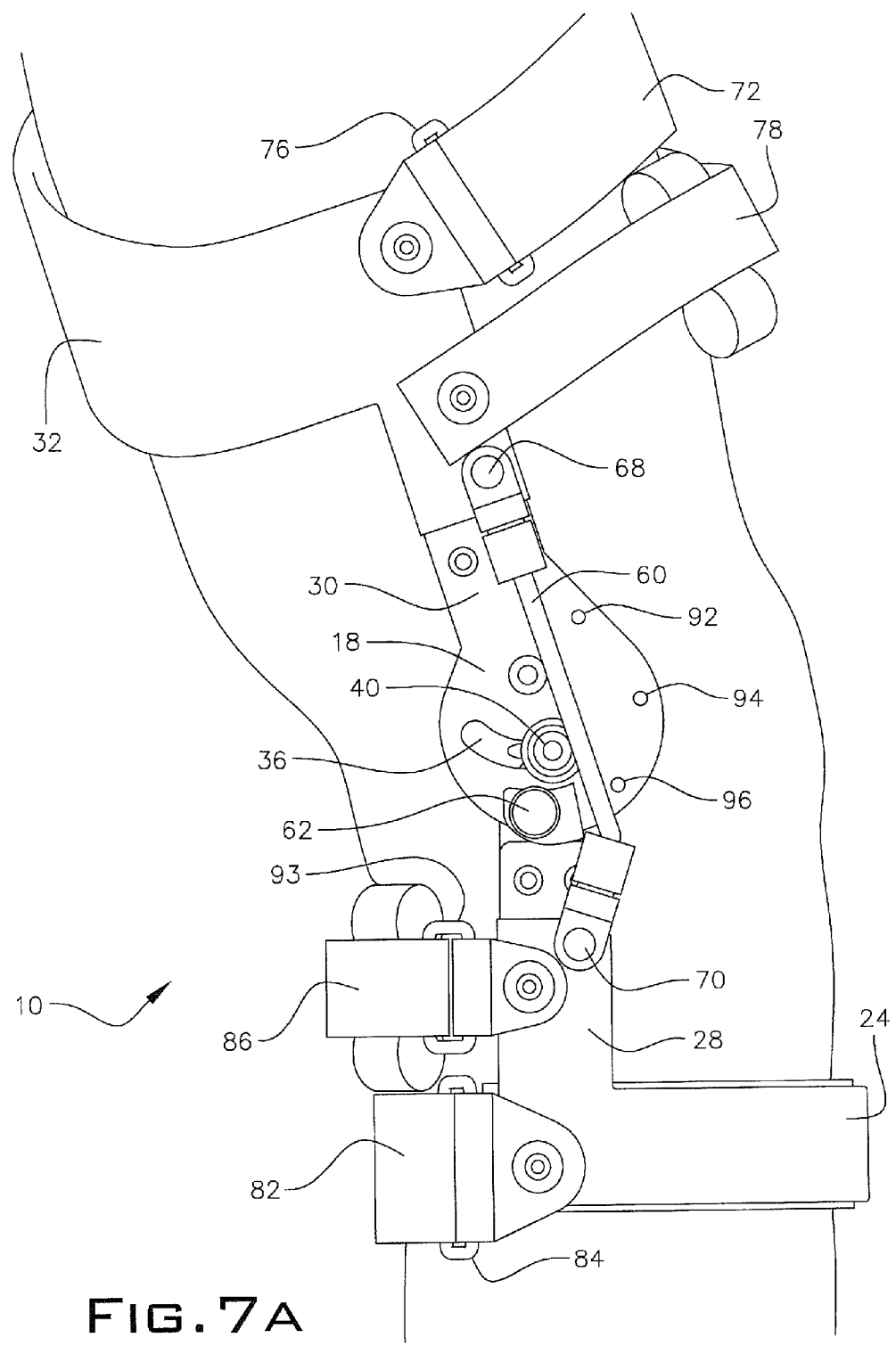
FIG. 7A is a lateral side view of a knee brace hinge assembly and the novel swing assist mechanism of FIG. 1 on an extended leg of a patient with only one fulcrum block in place.
Figure 7B:
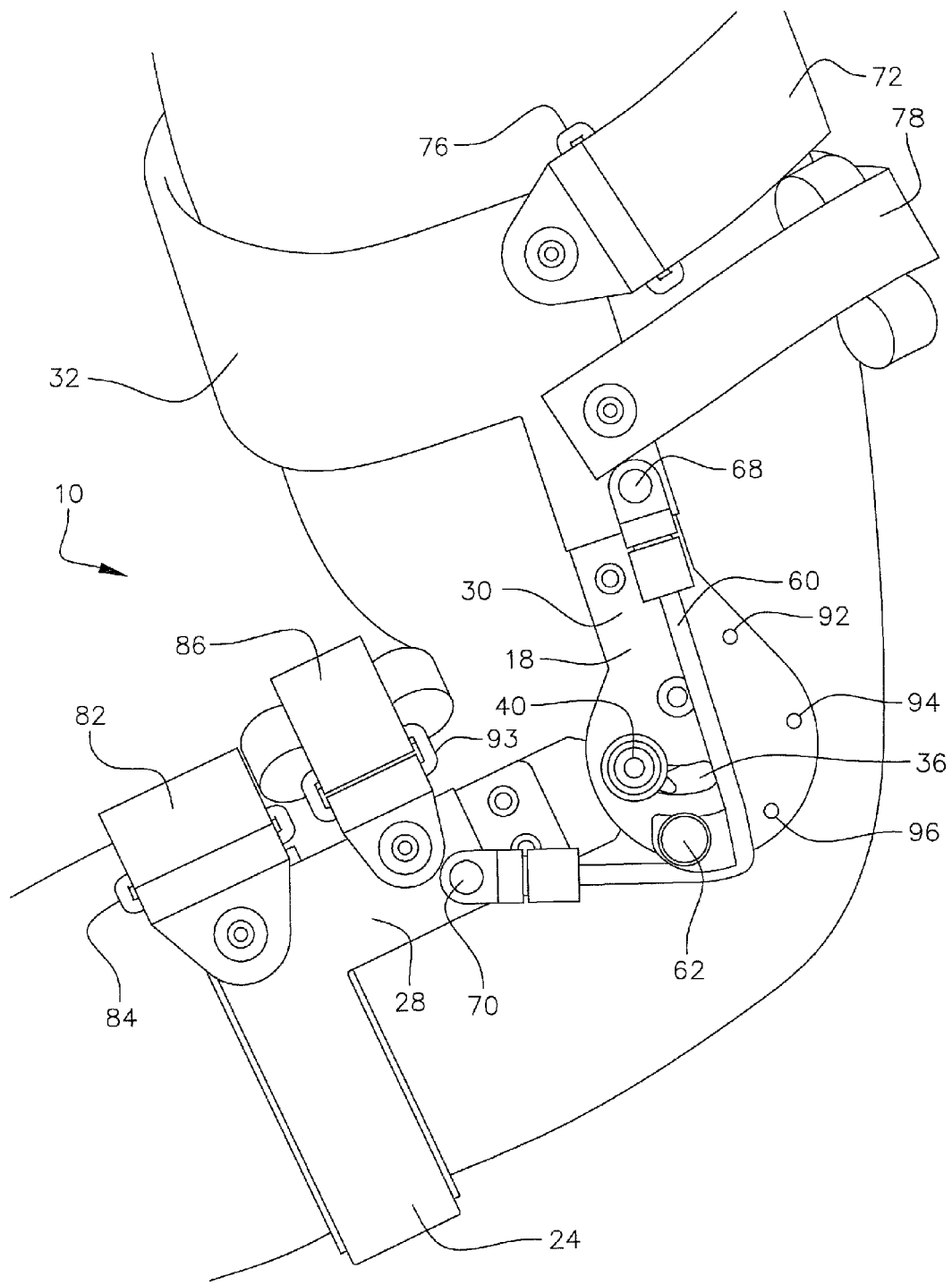
FIG. 7B is a lateral side according to FIG. 7A with the patient's knee bent.

FIGS. 7A and 7B show minimal alignment using only one fulcrum block 62 on the polycentric hinge 18.

Figure 8A:
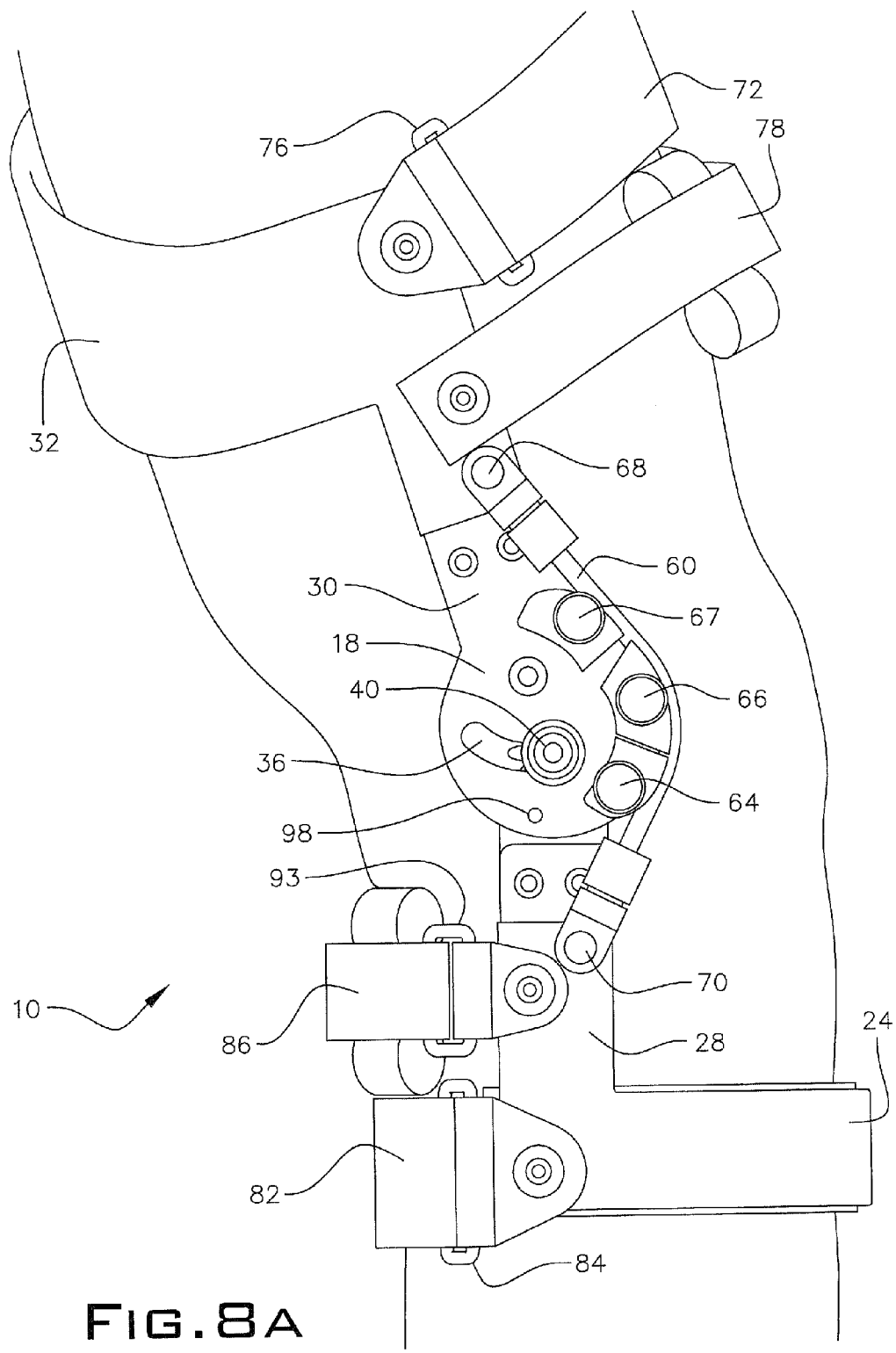
FIG. 8A is a lateral side view according to FIG. 1 on an extended leg of a patient with the fulcrum blocks moved to an extreme position.
Figure 8B:
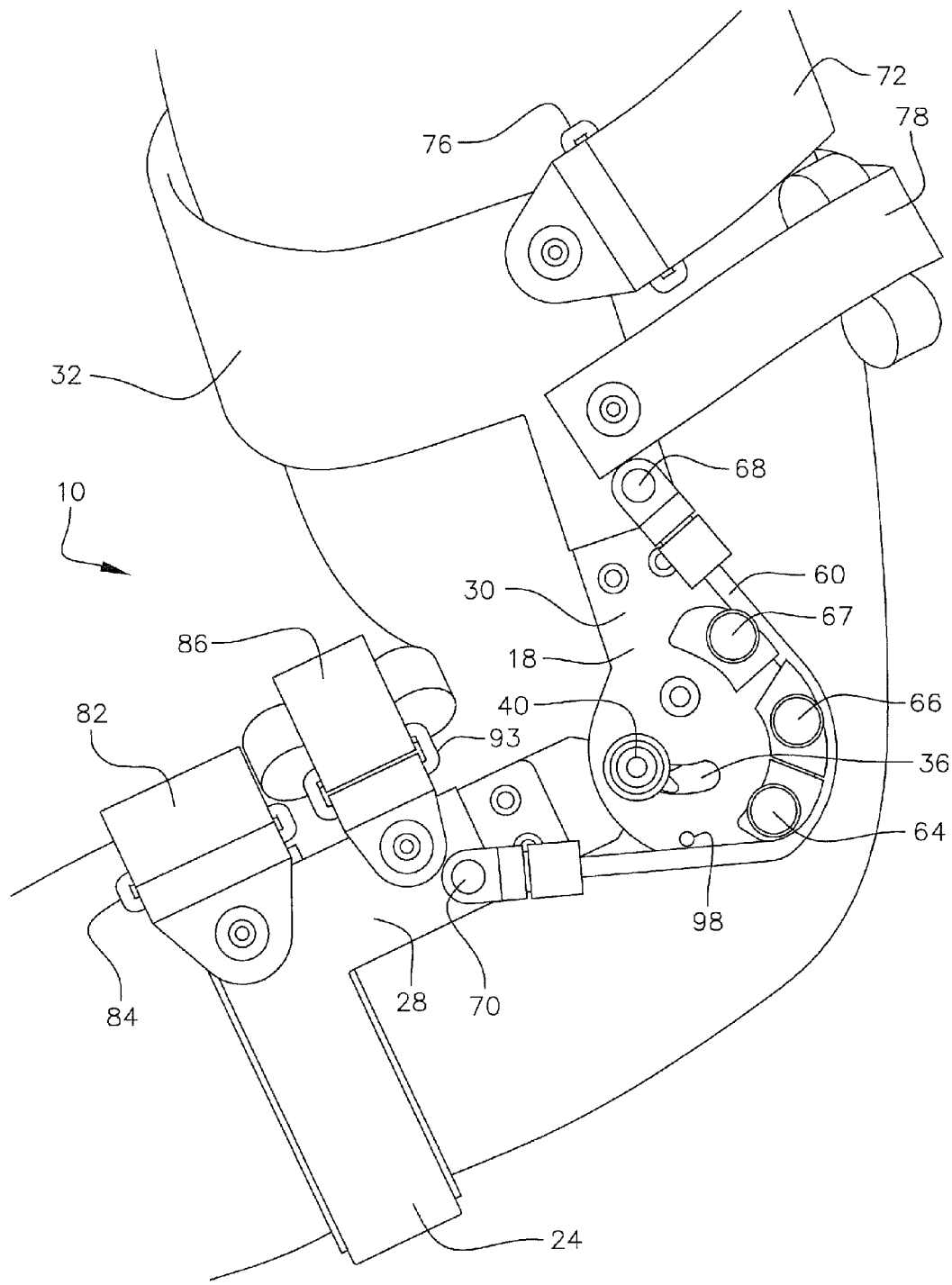
FIG. 8B is a lateral side view according to FIG. 8A with the patient's knee bent.

FIGS. 8A and 8B show an extreme alignment using fulcrum blocks 64, 66 and 67. In this condition there is no fulcrum block 62 in lower aperture 98 on the polycentric hinge 18.

A strap 72 tightens thigh cuff 32 in place.

A second mid-thigh cuff securing strap 78 is a soft elastic material with a soft adjustable pad 74 placed at the inner midpoint area of strap 78. Strap 72 is placed through a D-ring fastener 76 on the side of the thigh cuff 72. Hook and loop material is used to engage strap 72 to itself. Soft padded mid-thigh securing strap 78 travels from the lateral side of OA 10 through a second D-ring fastener 80 on the medial side of OA 10. The strap 78 fastens to itself by hook and loop material.

A shin cuff soft elastic material securing strap 82 travels across the back of the patient's calf through a third D-ring fastener 84 on the lower end of the lateral upright 28 and fastens onto itself with hook and loop material. A padded calf strap 86 travels around the back of the calf with an adjustable pad 88 located at mid strap 86. Strap 86 passes through a D-ring fastener 93 on the lower upright 28 and is attached to itself by hook and loop material.

The knee brace bends with free moving axial hinges, each with six equivalently sized axial teeth on the upper and lower aspects of the inner hinge assembly of the medial and lateral hinges 12 and 18. As the knee bends, the bend movement is tracked or guided by the rigid brace uprights at the hinge center axle through groove 36 on the lateral hinge. The hinge alignment forces the bend line of the brace through grooves 36 that is pre-cut into the lateral hinge 18. The specific bend movement of the knee is controlled by the hinge axle traveling through the grooves 36 in the lateral hinge 18. The adjustable dynamic fulcrum on the lateral hinge 18 can be set to provide a dynamic assist mechanism using fulcrum blocks 62, 64 and 66 with elastic band 60 to assist in controlling the alignment and movement of the knee from 20° of flexion to full extension of the knee. The adjustable properties of the dynamic fulcrum offer the fitter or wearer multiple settings to maintain knee joint space balance, improved knee joint alignment, and prevention of "reverse Screw Home Mechanism" or controlled rotation of the knee as the knee goes from 20° flexion to extension.

The adjustable elastic band 60 is on the lateral upright of the OA Knee Brace 10 for medial compartment osteoarthritis. Four threaded holes 92, 94, 96 and 98 are arranged along the hinge of the outer lateral connector plate 34. Fulcrum blocks 62, 64, 66 and 67 are screwed into the holes as needed. Fulcrum block 64 can be inserted in hole 96 providing the center point of the elastic band fulcrum as the knee bends if the optimal dynamic setting of the adjustable pull mechanism is needed. A second fulcrum block 62 with elastic band 60 tracking material can be inserted into threaded hole 98 if another optimal dynamic setting of the adjustable pull mechanism is needed. A third adjustable dynamic fulcrum mechanism is available by inserting fulcrum block 66 with the elastic band 60 tracking material into threaded hole 94. By providing three or more incrementally stronger or more elastic bands, the fitter will have multiple settings to adjust the dynamic fulcrum to maintain the correct amount of dynamic force to maintain optimal joint space on both the medial and lateral compartments of the knee as well as to maintain optimal knee alignment during the motion of the knee during ambulation.

It is understood that an OA knee brace having two uprights has been used above to describe a first embodiment of the swing assist mechanism of the present invention. Other knee braces can be used with the present invention having one or two uprights and if two uprights are employed, then the uprights are not offset. Further, swing assist mechanism can be attached to the outer side of a brace hinge, made integral with a brace hinge or made integral with one or more brace uprights.

Other equivalent elements can be substituted for the elements disclosed herein to produce the same results in the same way by the same manner.

The invention claimed is:

1. A knee orthosis device comprising:
at least one upright strut attached to upper and lower cuff members of said knee orthosis for securing said knee orthosis to a knee joint area of a patient, a dynamic gait swing assist mechanism comprising an adjustable portion and upper and lower fulcrum points, each of the upper and lower fulcrum points attaching opposing ends of an elastic band, the elastic band stretching over the adjustable portion;
a hinged portion within each of the at least one upright strut;
the elastic band directly interacting with the hinged portion, such that bending the hinged portion causes stretching of the elastic band, and straightening of the hinged portion relaxes the elastic band; and
wherein the elastic band acts to aid in extension of a knee joint of the patient during straightening of the hinged portion to correct the patient's gait wherein the adjustable portion includes at least one fulcrum block, the at least one fulcrum block interacting with the elastic band to increase force created by the elastic band, resulting in additional aid for extension of the knee joint of the patient.

2. The knee orthosis device of claim 1, wherein the elastic band is interchangeable.

3. The knee orthosis device of claim 1, wherein adjustable portion includes four fulcrum blocks.

4. The knee orthosis device of claim 3, wherein the four fulcrum blocks are interchangeable to provide a multitude of various setting tensions, and the four fulcrum blocks include a first fulcrum Nock, a second fulcrum Nock, a third fulcrum Nock, and a fourth fulcrum Nock.

5. The knee orthosis device of claim 1, wherein the dynamic gait swing assist mechanism is mounted either on the medial or lateral side of the knee joint area.

6. The knee orthosis device of claim 1, wherein the dynamic gait swing assist mechanism is mounted along an outer side of a knee orthosis hinge.

7. The knee orthosis device of claim 1, wherein the dynamic gait swing assist mechanism is integrally constructed within a knee orthosis hinge.

8. The knee orthosis device of claim 1, wherein the swing assist mechanism improves knee joint alignment during gait and corrects improper gait.

9. The knee orthosis device of claim 1, wherein the dynamic gait swing assist mechanism assists in controlling the alignment and movement of the knee joint from 20° of flexion to full extension.

10. A knee orthosis device comprising:
one or more upright members, each of the one or more upright members including a hinge and one or more cuff members, each of the one or more upright members having an aligned position and a bent position; and
an elastic band associated with, and attached to, one of the one or more upright members, the elastic band spanning across the hinge, the elastic band creating a force, the force acting to pull the associated upright member from the bent position to the aligned position;
the elastic band interacting with the hinge, the elastic band stretching when the hinge is bent, and relaxing when the hinge is straightened to aid in extension of a knee joint to correct gait wherein hinge further comprising one or more fulcrum blocks, the one or more fulcrum blocks cooperating with the elastic band to increase the force.

11. The knee orthosis device of claim 10 wherein the one or more upright member is a first upright member and a second upright member, and the elastic band is attached to only the first upright member.

12. The knee orthosis device of claim 10 wherein the one or more upright member is a first upright member and a second upright member, and the elastic band is attached to the first upright member and the second upright member.

13. The knee orthosis device of claim 10 wherein, the elastic band acts to improve knee joint alignment during gait and corrects improper gait.

14. The knee orthosis device of claim 10 wherein the elastic band is integral to the one or more upright members.

15. A knee orthosis device comprising:
at least one upright strut attached to upper and lower cuff members of the knee orthosis for securing the knee orthosis to a knee joint area of a patient;
a dynamic gait swing assist mechanism including upper and lower fulcrum points, an elastic band having an upper end and a lower end, and one or more fulcrum blocks, the dynamic gait swing assist mechanism acting to aid leg extension of the patient and correct the patient's gait, with the elastic band having a stretched position when a knee joint of the patient is bent, and a relaxed position when the knee joint of the patient is extended;
wherein the upper end of the elastic band connects to the upper fulcrum point, and the lower end of the elastic band connects to the lower fulcrum point; and
the one or more fulcrum blocks contact the elastic band, increasing a length of the elastic band during its extension from the relaxed position to the stretched position, thereby increasing its force.

16. The knee orthosis device of claim 15 wherein the elastic band is integral to the hinge.

17. The knee orthosis device of claim 15 wherein the elastic band is integral to the one or more upright members.

18. The knee orthosis device of claim 15 wherein the at least one upright strut is a first upright strut and a second upright strut, and the elastic band is attached to only the first upright strut.

* * * * *